United States Patent
Bonk et al.

(10) Patent No.: US 6,351,519 B1
(45) Date of Patent: Feb. 26, 2002

(54) METHOD FOR COMPENSATING THE DARK CURRENT OF AN ELECTRONIC SENSOR HAVING SEVERAL PIXELS

(75) Inventors: Roland Bonk, Stutensee; Uwe Zeller, Anspach, both of (DE)

(73) Assignee: Sirona Dental Systems GmbH, Bensheim (DE)

( * ) Notice: Subject to any disclaimer, the term of this patent is extended or adjusted under 35 U.S.C. 154(b) by 0 days.

(21) Appl. No.: 09/485,449

(22) PCT Filed: Aug. 10, 1998

(86) PCT No.: PCT/EP98/05069

§ 371 Date: Feb. 11, 2000

§ 102(e) Date: Feb. 11, 2000

(87) PCT Pub. No.: WO99/08440

PCT Pub. Date: Feb. 18, 1999

(30) Foreign Application Priority Data

Aug. 11, 1997 (DE) .......................................... 197 34 717

(51) Int. Cl.$^7$ ................................................. H05G 1/64
(52) U.S. Cl. ..................... 378/98.8; 378/98.2; 378/207; 250/370.11; 250/370.09
(58) Field of Search ............................... 378/98.8, 98.2, 378/207, 40, 62; 348/162; 250/370.03, 370.11

(56) References Cited

U.S. PATENT DOCUMENTS

| | | | |
|---|---|---|---|
| 4,750,057 A | * 6/1988 | Suzuki et al. | 378/62 |
| 4,811,372 A | 3/1989 | Doebert et al. | 378/39 |
| 4,878,234 A | 10/1989 | Pfeiffer et al. | 378/40 |
| 5,519,437 A | * 5/1996 | Nelvig | 348/162 |
| 5,528,645 A | 6/1996 | Koivisto | 378/37 |
| 5,604,781 A | 2/1997 | Suzuki et al. | 378/62 |

FOREIGN PATENT DOCUMENTS

| | | |
|---|---|---|
| DE | 195 25 678 | 1/1996 |
| DE | 196 04 631 | 8/1996 |
| EP | 0 229 308 | 7/1987 |
| EP | 0 279 294 | 8/1988 |
| WO | WO 89/10037 | 10/1989 |
| WO | WO 93/23952 | 11/1993 |

OTHER PUBLICATIONS

Albert J. P. Theuwissen, "Solid–State Imaging with Charge–Coupled Devices," Kluwer Academic Publishers, Dordrecht, Boston, London, 1995, pp. 92–95, 274–275.

* cited by examiner

Primary Examiner—David P. Porta
Assistant Examiner—Pamela R. Hobden
(74) Attorney, Agent, or Firm—Foley & Lardner

(57) ABSTRACT

A method is proposed for compensating for the dark current of an electronic sensor having a plurality of pixels with an individual dark-current response, radiation for producing an image signal (BS) being directed from a beam source (3) onto a detector arrangement (4) containing the sensor, and a recording being taken with different clock-out rate (v) (integration time) by reading the detector signal (S) present in the pixels of the sensor, in which, before the beginning or after the end of the recording with radiation, the sensor is read out without radiation with at least two different clock-out rates ($v_1$, $v_2$) and at least two dark-current signals (DC1, DC2) are thereby picked up for each pixel, in which the dark-current signals (DC1, DC2) that have been read out are then used to calculate a dark-current value (DV) of individual pixels of the sensor as a function of the clock-out rate (v), and in which a correction is then made, using the dark-current value associated with each pixel, to the detector signal (S) with the dark-current signal superimposed on it in order to calculate the picture value (PV).

9 Claims, 3 Drawing Sheets

Figure 1:
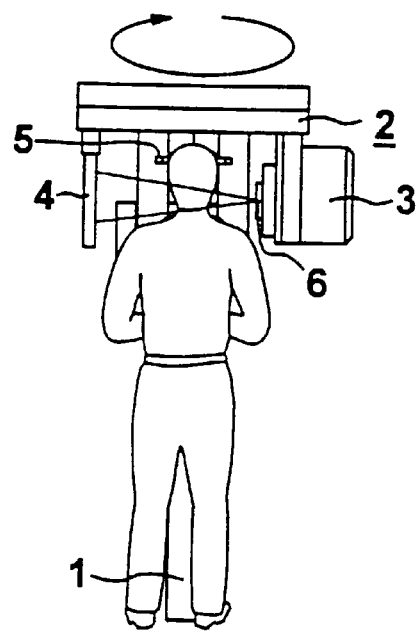

METHOD FOR COMPENSATING THE DARK CURRENT OF AN ELECTRONIC SENSOR HAVING SEVERAL PIXELS

The invention relates to a method of compensating for the dark current of an electronic sensor having a plurality of pixels. In this case, radiation for producing a picture signal is directed from a radiation source onto a detector arrangement containing the sensor, and a plurality of recordings are taken with different recording time (integration time) through reading out the detector signal present in the pixels of the sensor. A method of this type can, in particular, be used to make dental panorama or cephalometric tomographs with an X-ray diagnosis instrument that contains a rotation unit with a beam source and, arranged diametrically thereto, a detector arrangement having an electronic sensor, preferably a CCD sensor.

EP-A-0 279 294 discloses the use, in dental X-ray diagnosis technology, of a beam-sensitive (CCD) sensor in panorama or cephalometric X-ray tomographs instead of a film with an amplifier sheet, and the electronic "reconstruction" of the function of the moved film by a special type of operation of the sensor (TDI: time delay and integration), by correspondingly clocking forward the sensor's charge packets produced by the illumination while new charges are being continuously added.

DE-A-19 525 678 describes a method and a device for adjusting picture-generating values in an X-ray that produces a panorama X-ray. A disadvantage in this case is that the spatial dependency of the dark current in relation to the individual pixels, which is due to the manufacturing process, is not taken into account. Although a time dependency is implicitly provided by adjusting the signal-to-noise ratio, the described arrangement nevertheless assumes an ideal sensor which works without defects in the pixels.

In design terms, X-ray sensors generally consist of a plurality of (CCD) elements arranged with minimal separation. The picture signal produced by X-radiation has a plurality of noise signals superimposed on it. The dominant impairment to the signal is made by the time- and temperature-dependent generation of charge carriers in the sensor, which is referred to in the specialist literature "Solid State Imaging with Charge-Coupled Devices", Albert J. P. Theuwissen, Kluwer Academic Publishers Dordrecht, Boston, London 1995, pages 92–95 (and pages 274/275 as regards TDI operation) as a dark current. The dark-current signal which is generated depends both on the sensor used and on the individual pixels of the sensor; the dark-current signal is therefore spatially dependent [y]. Furthermore, this signal is dependent on the integration time and therefore also on the variable turning speed of the rotation system, and thereby time-dependent [x]. In addition to this, the dark-current signal is also dependent ion temperature and the lifetime-cumulative X-ray dose.

Hitherto, corrections for the dark current have been made by picking up dark-current information at the start and end of a recording from the covered, that is to say unexposed, edge regions of the sensor. A correction value is calculated for each row from the data obtained in this way. The associated correction value, constant over the entire row, is then subtracted from each pixel of a row.

A disadvantage with this type of dark-current correction is that although fluctuations in the integration time, and therefore the time-dependent variation in the dark current are taken into account, no fluctuations in the individual pixels on a row of the sensor are taken into account. Significant picture artefacts can therefore occur depending on the CCD sensor used.

Another known method of correcting for the dark current is to subtract a full dark-current recording. To do this, in addition to the recording of the picture, a dark-current recording is made and is subtracted from the radiation recording. Although such a method gives good results, it cannot be used for the panorama and cephalometric recordings mentioned at the start since costs would be disproportionately increased through the dark-current picture and the concomitant storage costs additionally required. Furthermore, the recording procedure would be slowed by the required delay made necessary by the generation of position pulses.

WO-A-8 910 037 discloses a method and a device for compensating for the dark current and a base-value shift in the voltage of a CCD unit, in which a control process is used whose manipulated variable is derived from CCD cells arranged covered. This procedure is repeated continuously for each row of the linear CCD and the dark-current information of the covered CCD cells is used for correction of CCD cells arranged physically at other positions. In this case, the integration unit is operated with two time constants. To that end, the signals from CCD cells arranged covered are amplified and converted into digital signals. In a comparator unit, the digital values are compared with a predetermined value. If the value coming from the covered cells is too high, then the time constant of the integration unit is reduced. If the digitized value approaches the optimum, then the integration unit is operated with a large time constant, which results in faster read-out. It is furthermore proposed to assign the integration units a time constant which is so high that the amplified output signal remains approximately constant during the read-out of a row from the CCD unit. It is nevertheless possible to switch over the time constant of the integration unit from a first to a second position with smaller time constant, in order to implement the control loop, when the situation is far from the optimum dark-current compensation, as is the case for example when warming up the instrument or in the event of a significant variation in ambient temperatures.

A disadvantage here is also that only the CCD cells arranged covered are used for information about the dark-current profile and for the required dark-current compensation, rather than the CCD cells themselves actually used for recording the picture. Furthermore, the time taken to compare the digital values with a predetermined value at the start of each picture row leads to a delay in which no picture data are picked up.

The object of the present invention is to obtain an improved way of compensating for the dark current.

According to the invention, before the beginning or after the end of a recording with radiation, the sensor is read out without radiation using at least two different clock-out rates (integration times), and at least two dark-current signals are thereby picked up for each pixel. The dark-current signals that have been read out are then used to calculate a dark-current value of the individual pixels as a function of the clock-out rate and the calculated dark-current value available for each pixel is thereby calculated. This dark-current value is lastly used for picture correction by subsequently using the dark-current value associated with each pixel to make a correction to the detector signal with the dark-current signal superimposed on it in order to calculate the picture value.

Advantageously, a CCD sensor is driven using this method, in particular the operation of a two-dimensional pixel matrix in TDI mode being especially advantageous.

The sensor may in this case have a plurality of regions spatially separated from one another, between which no signal need necessarily be picked up. This non-radiation-sensitive region is advantageously minimal, approximately of the order of a pixel. It is thereby possible to produce a sensor composed of a plurality of regions. The response, deviating in particular in the edge region of each region in comparison with the central regions, can be corrected using the method according to the invention.

For calculating the dependency of the dark-current value on the clock-out rate, a computed relationship is produced with the aid of the at least two dark-current signals that are read out, and the dark-current value assigned to a pixel is calculated by means of a computed relationship corresponding to an inter- or extrapolation as a function of the actual recording time. The number of double-current signals read out for each pixel can be regarded in mathematical terms as a number of support points for ascertaining a computed relationship. The dark-current response of a pixel is in this case defined by an approximation, and the dark-current value of a pixel is expressed as a function of the integration time as a first-order equation, which is defined by two support points, or as a higher-order fitting function, if more than two support points are picked up.

In order to ascertain the integration times of the individual picture columns, the times of the clock-out pulses and therefore the clock-out frequency are picked up and kept. The integration time of a picture column in TDI operation is the sum of the respective last (n) ascertained clock-out times, (n) in this case defining the number of pixels in the TDI direction. The number of clock-out times depends on the width of the sensor and therefore on the number of pixels in a column. In a fictitious sensor with for example a 66 pixel width (in the TDI direction), 66 integration pulses are obtained. The integration times are calculated for each picture row from the preceding 66 integration rows and are stored.

The method is suitable, in particular, for taking a dental X-ray recording, since in this case a non-constant speed of motion of the sensor leads to different clock-out rates (integration times) of the sensor.

Advantageously, the method according to the invention is used to take dental panorama or cephalometric tomographs with an X-ray diagnosis instrument that contains a rotation unit with a beam source and, arranged diametrically with respect to it, a detector arrangement having at least one electronic sensor. During these recordings, the rotation unit is turned at a non-constant speed of motion around the patient's head.

The detector signals obtained when the sensor is being read out are advantageously stored in a memory unit. In a subsequent step, correction to the detector signal with the dark-current signal superimposed on it is made in order to calculate the picture signal in a computer unit connected to the memory unit. By means of this, the compilation of the corrected recording after the generation of the uncorrected recording is decoupled from the actual recording process, so that the recording itself is not affected by the correction.

In principle, however, it is also possible to pick up the dark-current signals before the start of the recording and carry out real-time correction, so that picture values can be displayed actually during the recording.

Figure 2:
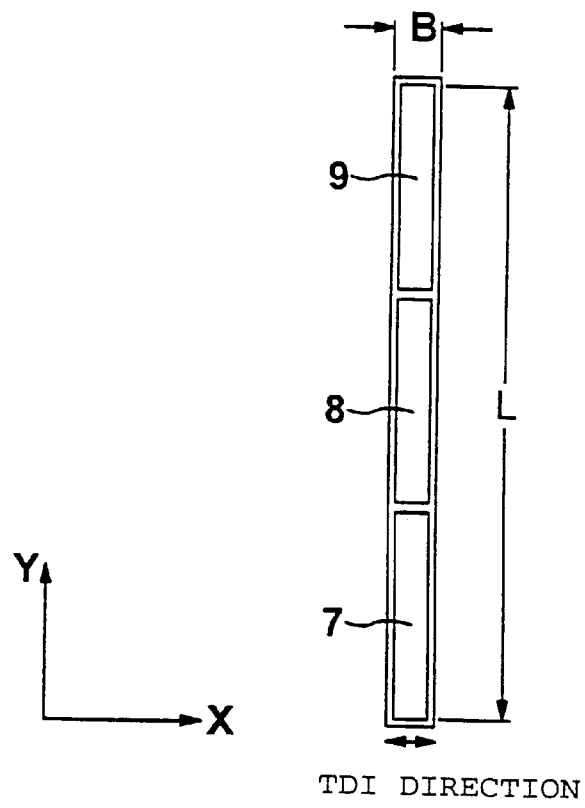
Figure 3:
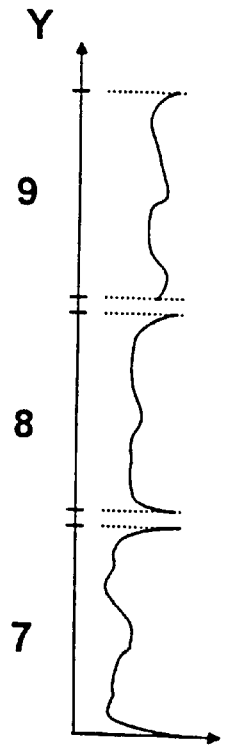
Figure 4:
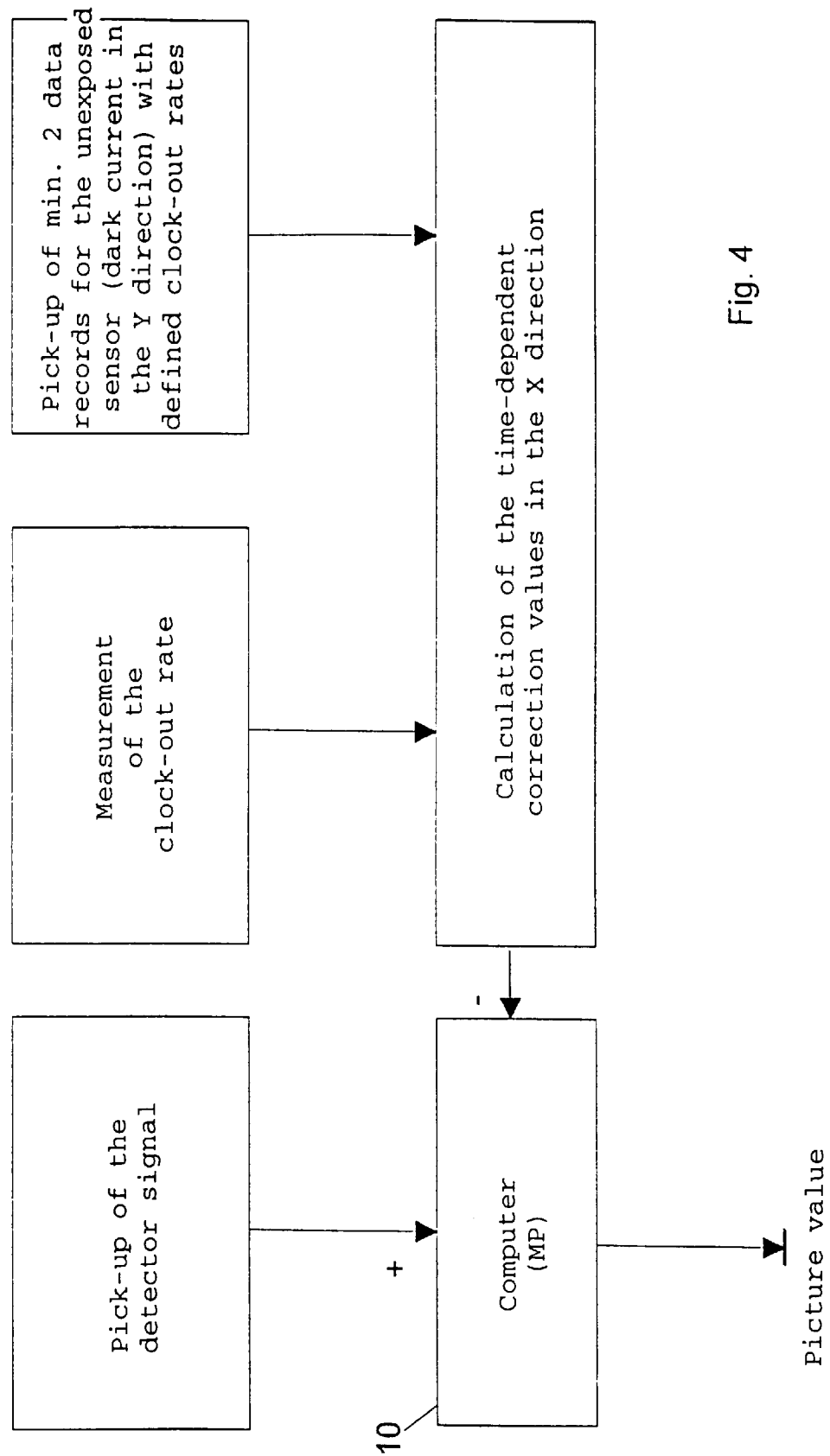
Figure 5:
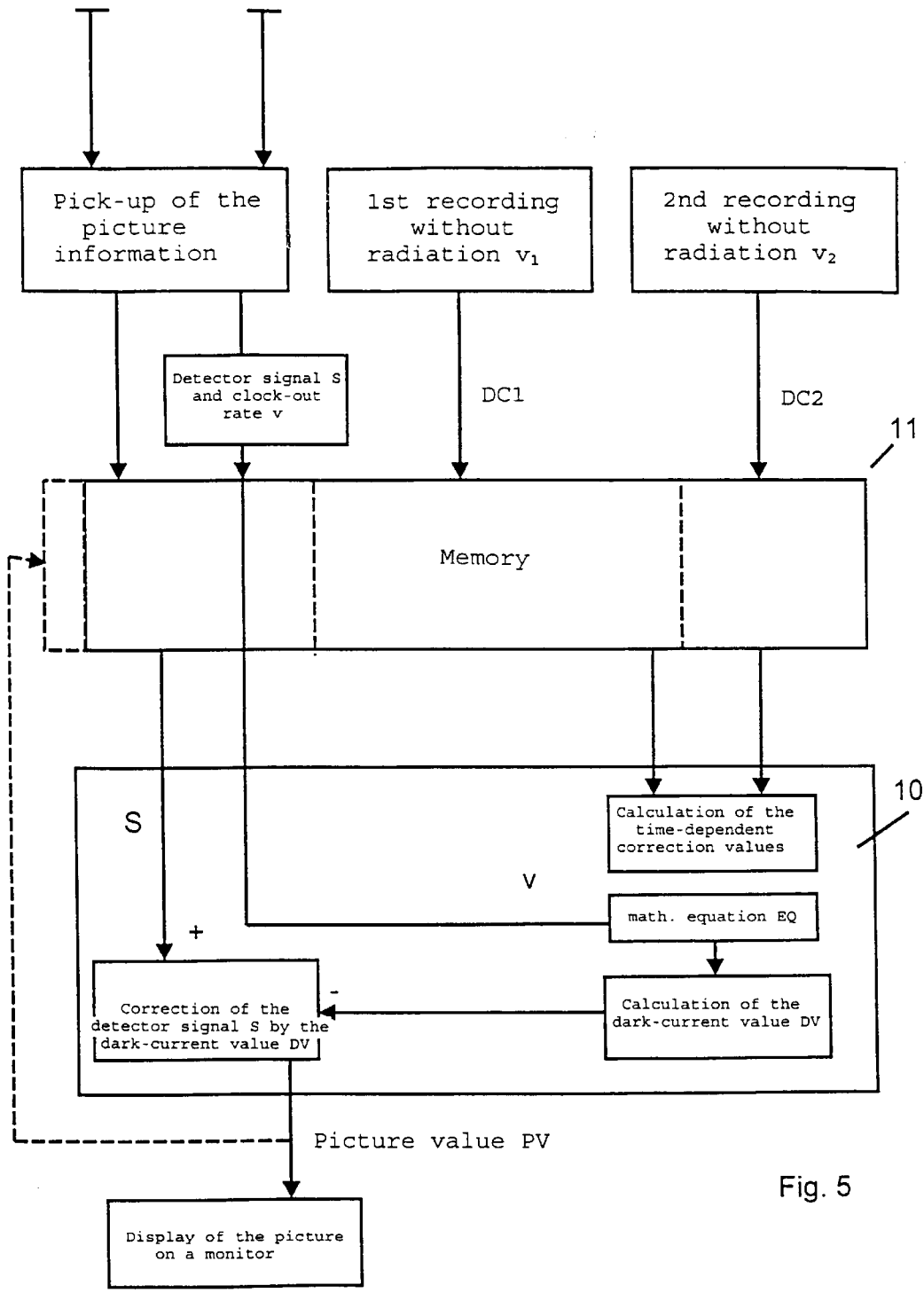

The procedure is explained in more detail with the aid of FIGS. 1 to 5, in which:

FIG. 1 shows an outline presentation of a dental X-ray diagnosis instrument for picking up panorama tomographs, FIG. 2 shows a detector arrangement with a sensor having a plurality of regions, FIG. 3 shows a dark-current profile made up of the dark-current values of a row of pixels of the detector arrangement in FIG. 2, FIG. 4 shows a first flow chart with the basic principle of the invention, and FIG. 5 shows a flow chart involving the use of a memory.

FIG. 1 shows an outline representation of a dental X-ray diagnosis instrument for picking up panorama tomographs, abbreviated to PAN recordings below. The instrument contains a height-adjustable support column 1 holding a rotation unit 2 that supports, on one side, an X-ray source 3 with a primary diaphragm 6 and, diametrically with respect to it, on the other side, a detector arrangement 4. 5 denotes a retaining and positioning device for the head, using which the patient's head can be fixed in a defined position in known fashion. The structure and possible adjustments of the rotation unit and the retaining and positioning device for the head are known and are described, for example, in EP-0 229 308.

The detector arrangement 4 contains three X-ray-sensitive CCD elements 7 to 9 (FIG. 2) which have a specific width (B) and length (L) and are arranged at a small distance one above the other. For PAN recordings, the CCD width (x direction) is typically 5 to 10 mm, and the sensor length (y direction) is in all 150 mm. The TDI direction, in which the charge packets are transported within the CCD, is indicated by an arrow. A plurality of pixel rows are arranged next to one another in the width direction.

FIG. 3 represents the dark-current profile actually existing for a row of pixels of the CCD elements 7 to 9, with the aid of the dark-current values DC of each individual pixel of the CCD elements 7 to 9. The dark-current values of the individual pixels can differ considerably from one another, and so the profiles can differ greatly from one another. Due to manufacture, high dark-current values exist especially in the edge region, since the sawing of the sensor material causes changes in the material. Discontinuities therefore arise in the region of the junctions between two neighboring CCD elements 7, 8, 9.

As can be seen from the flow chart according to FIG. 4, the acquired picture information, in the form of the detector signal S, consisting of the integrated picture signals PS with the dark-current signals DC, is read out and sent to a computer 10. At the same time, the associated clock-out rates are measured and kept. As mentioned above, before the start of a recording or after a recording, at least two data records are picked up from the unexposed sensor with defined clock-out rates $v_1$, $v_2$. The information obtained in this way is subjected to a calculation by approximation, a dark-current value DV calculated for each pixel being in this case determined. In conjunction with the integration times, time-dependent correction values are ascertained and are made available to the computer 10 in order to compensate for the dark current. The computer 10 then delivers picture values PV which are improved in terms of dark-current response and, in known fashion, are processed to form a picture that can be reproduced on a monitor in known fashion.

In FIG. 5, the flow chart is refined by providing a memory unit 11 in which the picture information, consisting of the picture signal PS and the dark-current signal DC, are stored as a detector signal S with the clock-out rate v being picked up. The memory 11 also stores the dark-current signal DC1, DC2, belonging to each pixel, for the at least two recordings with different clock-out rates $v_1$, $v_2$, which are used to calculate the time-dependent dark-current value DV in order to correct the detector signal S. Through the clock-out rate v, a direct relationship with the integration time is arranged, since for a high clock-out rate v the integration time is low, and vice versa. The clock-out rate itself has a relationship with the rate of motion of the sensor.

In the computer 10, the dark-current value DV is calculated as a function of the integration time, the dark-current signals DC1, DC2 being employed to produce a first-order equation and the dark-current value DV being ascertained by inter- or extrapolation. If the number of recordings without radiation with different clock-out rates $v_1, \ldots v_n$ increases, then the number of support points increases so that a higher-order mathematical equation can be produced.

In order to correct the detector signal, the dark-current value DV associated with the clock-out rate v is then calculated using the mathematic equation EQ for each pixel, the dark-current value DV being subtracted from the detector signal S. The picture value PV calculated in this way is displayed on a monitor 12 and, if appropriate, stored in the memory 11. The picture value can, of course, also be printed directly or used in a different way.

What is claimed is:

1. A method for compensating for the dark current of an electronic sensor having a plurality of pixels with individual dark current responses, comprising:

irradiating the electronic sensor;

reading detector signals (S) generated by pixels of the sensor at a clock-out rate (v);

reading at least two dark current signals (DC1, DC2) for each pixel, the dark current signals corresponding to clock-out rates ($v_1$, $v_2$);

calculating a dark current value (DV) for each pixel at clock-out rate (v) using the dark current signals (DC1, DC2) read at the clock-out rates ($v_1$, $v_2$); and correcting the detector signals (S) using the dark current value (DV) associated with each pixel to determine picture values (PV).

2. A method according to claim 1, wherein the electronic sensor from which the measurement signals are read out is a CCD sensor.

3. A method according to claim 1, wherein the sensor has a two-dimensional pixel matrix and is driven in TDI mode.

4. A method according to claim 1, wherein the detector signals (S) are generated using a sensor divided into a plurality of regions spatially separated from one another.

5. A method according to claim 1, wherein for calculating the dependency of the dark-current value (DV) on the clock-out rate (v) with the aid of the at least two dark-current signals (DC1, DC2) that are read out, a computed relationship is produced, and the dark-current value (DV) assigned to a pixel is calculated by means of an inter- or extrapolation corresponding to the computed relationship as a function of the actual clock-out rate.

6. A method according to claim 1, wherein the detector signals (S) represent a dental X-ray.

7. A method according to claim 1, wherein dental panorama or cephalometric tomographs are taken using an X-ray diagnosis instrument which contains a rotation unit having the beam source and, arranged diametrically with respect to it, the detector arrangement having at least one electronic sensor.

8. A method according to claim 1, wherein the detector signals (S) obtained when reading out the sensor are stored in a memory unit, and correcting the detector signals (S) with the dark-current signal (DC) superimposed on it to determine the picture values (PV) is carried out in a subsequent step in a computer unit connected to the memory unit.

9. A method according to claim 1, wherein the at least two dark-current signals (DC1, DC2) are read before reading the detector signals (S), and a dark-current value (DV) is calculated during the recording with the aid of the clock-out rate (v), and the detector signals (S) are corrected by the dark-current value (DV) and the picture values (PV) thus obtained are displayed and/or stored.

* * * * *